United States Patent [19]

Dudzinski et al.

[11] 3,974,208

[45] Aug. 10, 1976

[54] AMPHOTERIC SURFACE-ACTIVE AGENTS

[75] Inventors: Zdzislaw W. Dudzinski, Clifton, N.J.; Reginald L. Wakeman, Paris, France

[73] Assignee: Millmaster Onyx Corporation, New York, N.Y.

[22] Filed: Jan. 19, 1976

[21] Appl. No.: 650,539

Related U.S. Application Data

[60] Division of Ser. No. 594,550, July 9, 1975, which is a continuation-in-part of Ser. No. 429,681, Dec. 28, 1973, abandoned, which is a continuation-in-part of Ser. No. 98,144, Dec. 14, 1970, abandoned.

[52] U.S. Cl. ............................. 260/501.11; 252/8.8; 252/136; 252/546; 252/554; 252/DIG. 7; 252/DIG. 13; 260/501.13; 260/534 C; 260/DIG. 9; 424/70; 424/319
[51] Int. Cl.$^2$ ....................... C07C 101/12
[58] Field of Search ....... 260/534 C, 501.11, 501.13

[56] References Cited
UNITED STATES PATENTS

| | | | |
|---|---|---|---|
| 2,468,012 | 4/1949 | Isbell | 260/501.11 |
| 3,287,411 | 11/1966 | Wakemann et al. | 260/501.13 |
| 3,600,318 | 8/1971 | Mast | 260/534 R |

FOREIGN PATENTS OR APPLICATIONS
446,813   4/1936   United Kingdom............. 260/534 C OTHER PUBLICATIONS
Lange, "Handbook of Chemistry", 10th Ed. (1964), pp. 598, 599.

Primary Examiner—Joseph E. Evans
Attorney, Agent, or Firm—Arthur A. Jacobs

[57] ABSTRACT

This invention relates to amphoteric surface-active agents which have extremely powerful inhibitory action against Gram positive bacteria and which are substantially free from metal halide, and, particularly, sodium chloride. These compounds have the general structure:

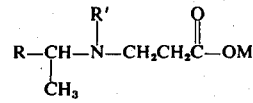

wherein R is a straight chain alkyl having from 6 to 16 carbon atoms, R' is a lower alkyl, and M is either hydrogen, an alkali metal or an alkylolamine.

2 Claims, No Drawings

AMPHOTERIC SURFACE-ACTIVE AGENTS

This is a division of co-pending application Ser. No. 594,550, filed July 9, 1975, which was a continuation-in-part of application Ser. No. 429,681, filed Dec. 28, 1973, and now abandoned, which, in turn, was a continuation-in-part of application Ser. No. 98,144, filed Dec. 14, 1970, now abandoned.

This invention relates to amphoteric surface-active agents and the process of making such agents from materials commercially available at low cost; and it particularly relates to surface-active agents of the aforesaid type which are extremely active against Gram positive bacteria and are substantially free from metal halide, particularly sodium chloride. They are useful for a variety of purposes.

The products of this invention contains a tertiary amino group attached to the 2-carbon of a long chain alkyl, and a carboxyethyl group substituent on the nitrogen atom.

The compounds of the invention have in general the structure:

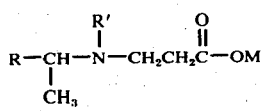

wherein R is a straight chain alkyl having from 6 to 16 carbon atoms; R' is a lower alkyl, such as methyl or ethyl; and M is either hydrogen, an alkali metal or an alkylolamine radical, such as mono-, di-, or tri-ethanol, or propanol amine radicals.

These compounds may be readily prepared by the reaction of an N-lower-alkyl-N-2-alkylamine with either acrylonitrile, an acrylate or acrylic acid, and are preferably prepared from alpha-olefins by methods known to the art; as for example, those described in U.S. Pat. Nos. 3,287,410; 3,287,411; 3,436,420; and 3,497,555. Alternatively, they may be prepared from 2-alkanols as well as other materials and by other reaction procedures, although it is preferred to prepare them from the very cheap and abundant alpha olefins such as are produced by a Ziegler type synthesis by polymerization of ethylene; or by the cracking of straight-chain paraffinic hydrocarbons.

Briefly, the procedures include hydrochlorination or hydrobromination in the presence of a catalyst such as $FeCl_3$ to produce the corresponding 2-haloalkanes in excellent yield; or by sulfating to produce the 2-alkyl sulfates. In either case, the intermediate products are then reacted with methylamine or ethylamine under pressure to yield the corresponding N-lower alkyl N-2-alkylamines.

More specifically, the amphoteric surface-active agents of the present invention may be prepared by reacting the aforesaid secondary 2-amines with, for example, acrylonitrile, followed by hydrolysis of the resulting alkylamino propionitriles to the corresponding N-lower alkyl-N-2-alkylaminopropionic acids, or by saponification with a calculated quantity of base to their alkali metal or alkylolamine salts. Instead of acrylonitrile, acrylic acid or an acrylate, more specifically a lower alkyl acrylate such as ethyl acrylate or the like may be substituted. Instead of the acrylics, β-propiolactone may be employed. The proportion of the acrylic compound relative to the secondary amine is preferably about mol per mol or a moderate excess of the acrylic. The excess speeds the reaction, but is not essential. Reaction with acrylonitrile or methyl or ethyl acrylate may be conducted at a temperature of between 100° and 140°C and at a pressure of between 10 psi and 60 psi, as developed; alternatively, the reaction may be carried out at atmospheric pressure by gradual addition of the acrylic reagent below the surface. At about 100°C, the reaction is unnecessarily slow; about 130°C is preferred, to avoid polymerization of the acrylic.

Reaction with acrylic acid may be conducted in aqueous medium at about 85°–95°C at atmospheric pressure.

Beta propiolactone reacts with the 2-amines at about 60°–120°C at atmospheric pressure, as shown in the following Example 7.

The products so obtained are of value in a multiplicity of applications. In this respect, because of their efficacy in strongly acid solution, they may be employed in pickling or other metal treating operations. They are also useful textile assistants, either by themselves or with other agents. They may also be used as dye levelers, softeners and wetting agents. In addition, they are effective emulsifying agents. Because of their amphoteric character, they may be combined with quaternary ammonium or with phenolic and other germicides and pesticides. An important aspect of the present invention is the employment of these products in cosmetic preparations; for example, in combination with sulfated fatty alcohols and the like, they make excellent shampoos and bubble baths.

An essential consideration, especially when the product is used in cosmetic formulations such as shampoos and the like, is the absence of metal salts. There are two reasons for this: (a) metal salts, such as sodium or potassium chloride, act as thickening agents in shampoos and the like; tending to cause significant thickening at concentrations as low as 0.05 to 2.0% by weight, depending on the system, so that if a surfactant contains, for example, 0.7% and is used in concentrations of 30% by weight, the final product would contain 0.2% by weight salt and would render the product too viscous to provide sufficient flexibility in the preparation of the desired formulation; and (b) metal salts such as sodium and potassium chloride are irritants to both the skin and eyes if present in significant proportions, as, for example, above 0.5% by weight.

Prior processes for preparing compounds of this general type have usually resulted in the formation of excessive metal salts which could not be satisfactorily removed. For example, in one such process, the amine is dissolved in ethyl alcohol, heated to 70°–80°C and then reacted with sodium monochloracetate. Sodium chloride is produced. However, even with the greatest care in filtration, applicants could not reduce the concentration of sodium chloride to less than 2.08% by weight, as determined by potentiometer titration with silver nitrate using a metallic silver electrode as the indicator and saturated potassium sulfate solution as the reference electrode. Even when anhydrous ethanol was substituted for the normal ethyl alcohol, the sodium chloride content could not be reduced to less than 0.7 to 0.8% by weight.

In accordance with the present process, where, for example, an acrylonitrile-amine condensate or an acrylic-ester-amine condensate is used, on hydrolysis the yield is only B-amino acid entirely free of metal salt. More specifically, the condensates are hydrolyzed with just enough sodium hydroxide to permit the hydrolyzation to take place. As a result, sodium chloride production is avoided.

In addition to their surface-active properties, the compounds of this invention have extremely powerful inhibitory activity against Gram positive bacteria. Therefore, they may be used in compositions which require an amphoteric surfactant, or inhibition of Gram positive bacteria; and they are particularly useful in compositions where both of these properties must reside in one component.

The following examples are illustrative of the present invention, without, however, limiting it except as claimed.

EXAMPLE 1

A crude grade of N-methyl-N-2-tetradecylamine was obtained from alpha tetradecene, in the manner taught in U.S. Pat. No. 3,436,420, by the successive steps of hydrochlorinating to 2-chlorotetradecane; and then aminating with methylamine, and stripping to remove most of the lower-boiling material. The residual product contained some small amount of unreacted olefin and chlorotetradecane, along with traces of N-methyl-N,N-di(2-tetradecyl) amine. The crude product was reacted with a slight excess of acrylonitrile as follows.

426 grams of the amine or 1.5 mol (by equivalent weight titration) and 90 grams or 1.7 mol of acrylonitrile were charged into an agitated pressure vessel wherein the mixture was heated to 130°–140°C for a period of seven hours; the initial pressure was about 60 psi, falling to about 18 psi towards the end.

Samples were removed at intervals, and were titrated to determine the amount of unreacted acrylonitrile by the mercaptan reaction method described in American Cyanamid Company's "The Chemistry o Acrylonitrile", (Second Edition, 1959) pgs. 61–62. After three hours, 7.3% of residual acrylonitrile was present; after five hours 3.0% and after seven hours, 2.8%. Conversion was essentially complete to N-methyl-N-2-tetradecyl-amino-beta propionitrile.

Fractional distillation at 2 mm. pressure yielded, after a forerun, a 98% pure product in 93% of the theoretical yield, distilling between 166° and 180°C.

A repetition of this procedure, but substituting a refined grade of N-methyl-N-2-tetradecylamine resulted in virtually 100% theoretical yield. In this respect, either this or the cheaper grade of amine may be employed for industrial scale applications.

EXAMPLE 2

71.5 grams or 0.25 mol of the 98% grade product of Example 1 was treated with 10.2 grams of 98% solid caustic soda in 10 grams of water and 5 grams of isopropanol, under reflux in an agitated round-bottom flask for two hours, at about 130°C and ambient pressure.

After cooling to 80°C, 70 grams of isopropanol was added, and the reflux condenser was replaced with a total-take-off condenser. The isopropanol was distilled off to remove traces of ammonia. After cooling, 150 grams of water and 40 grams of isopropanol were added. The concentration was adjusted to 40% active material as the sodium salt of N-methyl-N-2-tetradecyl-beta-amino propionic acid. This product was a viscous, straw-colored solution having an isoelectric point between 4.5 and 6.0.

EXAMPLE 3

In the same manner as in Example 1, the dodecyl-, hexadecyl- and octadecyl- homologs of N-methyl-N-2alkyl-beta-amino-propionitrile were prepared from either crude or refined grades of N-methyl-N-2-alkylamines. Heating times ranged from 7 to 14 hours, temperatures from 110° to 140°C, the pressures varying accordingly. In each case, yields of 90%–95% of theory were obtained of products of about 99% purity.

EXAMPLE 4

In a similar manner to that of Example 2, the nitriles of Example 3 were saponified, varying the amounts of alcohol and water, and, consequently, the reflux temperatures and the elapsed time. For example, 3 grams of the $C_{12}$ homolog was saponified with 20 grams of 50% caustic soda solution and 50 grams of isopropanol at 88°C under reflux for 13 hours: the $C_{16}$ homolog of 99% purity in the amount of 77.6 grams, with 10.2 grams of 98% solid NaOH and 50 grams of ethanol (SD 40) at 84°C for 7 hours; and the $C_{18}$ homolog of 99% purity in the amount of 169.5 grams with 20.4 grams of 98% solid NaOH, 80 grams of ethanol and 20 grams of water at 84°C for 11 hours. The concentration was adjusted to about 40% active material.

EXAMPLE 5

Instead of acrylonitrile, the N-methyl-N-2-alkylamines were reacted with acrylic acid, and also with acrylic esters such as methyl acrylates. The acrylic acid was inclined to produce small amounts of by-products; the acrylates are exceptionally desirable for their reaction characteristics, but are more costly than acrylonitrile. The end products are, however, the same. The reaction conditions for such esters as methyl acrylate or ethyl acrylate are substantially the same as for acrylonitrile.

EXAMPLE 6

214 grams of 93% active N-methyl-N-2-dodecylamine (1 mol), 72 grams or 1 mol of beta propiolactone and 100 grams each of water and isopropanol plus 53 grams of soda ash were heated together in an agitated, round-bottomed flask under reflux at ambient pressure for five hours at about 88°–90°C.

The product was a clear, light amber solution which remains completely soluble in acid and alkaline ranges of pH.

In the same manner the tetradecyl, hexadecyl and octadecyl homologs were prepared from the corresponding amines, heating from five to seven hours. All exhibited surface-active properties.

EXAMPLE 7

27 grams (or 0.1 mol) of N-methyl-N-2-hexadecylamine and 7.2 grams (or 0.1 mol) of acrylic acid, in 20 grams of distilled water and 15 grams of isopropanol, was heated under reflux at ambient pressure at about 85°–94°C, for 13 hours, to yield a clear, water-soluble product having surface-active properties. The other homologous amines reacted similarly.

EXAMPLE 8

The alkylaminopropionic acids of the preceding examples may be converted into the corresponding amine oxides:

$$R-\underset{\underset{CH_3}{|}}{\overset{\overset{R'}{|}}{CH}} - \underset{\underset{O}{\Downarrow}}{N} CH_2CH_2\overset{\overset{O}{\|}}{C} -OM$$

by treatment with a peroxide such as hydrogen peroxide, or with ozone. For example, 50.0 grams of N-methyl-N-2-hexadecyl-beta-amino-sodium propionate, 40% active solution, was adjusted to pH 9.7 with hydrochloric acid and 8.0 grams of 33% hydrogen peroxide was added, in an agitated round-bottomed flask. The charge was heated at 55°–60°C for three hours, during which time the pH dropped to 7.9 and the residual hydrogen peroxide was negligible.

On cooling, the product was a light colored viscous liquid, gelling at low temperatures.

In the same manner, 50.0 grams, of a 40% active solution of sodium N-methyl-N-2-tetradecyl-beta-amino propionate at pH 9.1 was heated with 9.1 grams of 33% hydrogen peroxide for two hours at 70°–80°C. The pH dropped to 5.9, and the excess hydrogen peroxide was minimal.

The light colored solution was less viscous than that of the 2-hexadecyl homolog.

EXAMPLE 9

Certain of the above preparations were tested for foaming properties in the Ross-Miles Foam Tester, at 0.25% active concentration in distilled water at 104°F, and at three pH levels, 4, 6 and 8. Among those tested were the 2-dodecyl, 2-tetradecyl and 2-hexadecyl derivatives of Examples 2 and 4; and also a 2:1 mixture of the dodecyl and tetradecyl, and 3:1 mixture of the tetradecyl and hexadecyl, at 0.25% total activity; these last being derived from available mixed alpha olefins.

Table 1

| Sample | pH | Initial | 1 Minute | 5 Minutes |
|---|---|---|---|---|
| 2-dodecyl | 4 | 220 | 45 | 0 |
| " | 6 | 230 | 180 | 5 |
| " | 8 | 220 | 150 | 15 |
| 2-tetradecyl | 4 | 225 | 200 | 165 |
| " | 6 | 235 | 220 | 195 |
| " | 8 | 230 | 205 | 185 |
| 2-dodecyl/tetradecyl | 4 | 210 | 200 | 150 |
| 2:1 ratio | 6 | 240 | 210 | 120 |
| | 8 | 250 | 210 | 20 |
| 2-tetradecyl/hexadecyl | 4 | 230 | 210 | 200 |
| 3:1 ratio | 6 | 230 | 210 | 115 |
| | 8 | 235 | 215 | 165 |
| 2-hexadecyl | 4 | — | — | — |
| " | 6 | 160 | 135 | 130 |
| " | 8 | 180 | 150 | 150 |

EXAMPLE 10

The foam building or stabilizing properties of the mixed 2-dodecyl/2-tetradecyl derivatives in mixture with an equal active weight of sodium lauryl sulfate, was tested in the Ross-Miles apparatus at 0.1% total active concentration in distilled water at 104°F. The separate 2-dodecyl and 2-tetradecyl derivatives and the sodium lauryl sulfate were also tested at 0.1% concentration, as well as the latter at 0.05% concentration.

Table II

| | ROSS-MILES FOAM HEIGHT IN MILLIMETERS | | | |
|---|---|---|---|---|
| Sample | pH | Initial | 1 Minute | 5 Minutes |
| 2-dodecyl | 6 | 255 | 220 | 215 |
| 2-dodecyl | 8 | 250 | 220 | 215 |
| 2-tetradecyl | 6 | 210 | 175 | 170 |
| 2-tetradecyl | 8 | 225 | 190 | 190 |
| 2-dodecyl/tetradecyl | 6 | 240 | 205 | 200 |
| 2-dodecyl/tetradecyl | 8 | 240 | 210 | 200 |
| Sodium lauryl sulfate 0.1% | 6 | 215 | 190 | 185 |
| | 8 | 215 | 185 | 180 |
| Sodium lauryl sulfate 0.05% | 6 | 190 | 160 | 160 |
| | 8 | 180 | 160 | 160 |
| 2-hexadecyl | 6 | 160 | 135 | 130 |
| 2-hexadecyl | 8 | 180 | 150 | 150 |

EXAMPLE 11

The products of this invention are effecting wetting agents. The standard Draves Wetting Test was applied at pH 6 and pH 8 at 75°F., in 0.1% active concentration - in distilled water:

Table III

| | DRAVES WETTING TIME IN SECONDS | |
|---|---|---|
| 2-alkyl Component | pH6 | pH8 |
| 2-dodecyl | 30.1 | 23.1 |
| 2-tetradecyl | 15.3 | 8.8 |
| Sodium lauryl sulfate | 12.9 | 11.5 |

EXAMPLE 12

A typical shampoo formula illustrative of the wide variety of uses was prepared as follows for the purpose of evaluating the shampooing effect on human hair (percentages are by weight of active content):

| | |
|---|---|
| 2-alkyl derivative | 2.7% |
| Diethanolamine lauryl sulfate | 11.8 |
| Lauric diethanolamide | 5.0 |
| Water to make | 100.0 |

The foaming test showed the following results:

Table IV

| | ROSS-MILES FOAM HEIGHT IN MILLIMETERS | | | |
|---|---|---|---|---|
| 2-Alkyl Component | pH | Initial | 1 Minute | 5 Minutes |
| 2-dodecyl | 6 | 240 | 210 | 205 |
| 2-dodecyl | 8 | 235 | 200 | 200 |
| 2-tetradecyl | 6 | 230 | 195 | 195 |
| 2-tetradecyl | 8 | 230 | 200 | 195 |

The following procedure was used to test the performance as a shampoo: five gram tresses of natural, brown European human hair, about eight inches in length, were first moistened by holding them under running tap water at 100°–105°F. An eye-dropper calibrated to contain 1 gram of the agent to be tested was charged with such solution, and this was applied dropwise to the suspended tress, from top to bottom.

A lather was worked up actively between thumb and forefinger, up and down for one minute; the quality of the lather was noted. The tress was then rinsed under running tap water at 100°–105°F. The shampoo and rinse were repeated a second time. The "Wet Comb Test" comprises combing the tress while wet and observing its manageability. This was repeated after airdrying overnight, as the "Dry Comb Test". The "Static Test", a measure of the tendence to develop static, is reported as the spread in inches of the lower end of the trees after such combing, measuring from the center to one side of the spread, in inches.

The quality of the lather and the ease of combing were rated as follows:
E = Excellent; VG = Very Good; G = Good;
P = Poor; VP = Very Poor:

Table V

| Component | Tress Test at pH 7 | | | Static Fly-away |
|---|---|---|---|---|
| | Lather | Wet Comb | Dry Comb | |
| 2-dodecyl | VG | P | P | 1" |
| 2-tetradecyl | VG | VG | E | ½" – 1" |

EXAMPLE 13

The amine oxides of Example 8 were also tested for foaming and wetting properties, at pH 4, 6, 8 and 10 respectively, in each case at 0.25% active content in distilled water, at 104°F, in the case of the Ross-Miles and at 75°F, in the Draves test.
They performed as follows:

Table VI

| ROSS-MILES FOAM HEIGHT IN MILLIMETERS | | | | |
|---|---|---|---|---|
| 2-Alkyl Component | pH | Initial | 1 Minute | 5 Minutes |
| 2-tetradecyl | 4 | 190 | 170 | 150 |
| " | 6 | 160 | 140 | 130 |
| " | 8 | 25 | 15 | 10 |
| " | 10 | 115 | 105 | 98 |
| 2-hexadecyl | 4 | 15 | 10 | 10 |
| " | 6 | 15 | 10 | 10 |
| " | 8 | 20 | 15 | 15 |
| " | 10 | 35 | 30 | 30 |

Table VII

| DRAVES WETTING TEST | | |
|---|---|---|
| 2-Alkyl Component | pH | Seconds |
| 2-tetradecyl | 4 | 8.3 |
| " | 6 | 8.3 |
| " | 8 | 12.6 |
| " | 10 | 8.8 |
| 2-hexadecyl | 4 | 17.0 |
| " | 6 | 45.8 |
| " | 8 | 63.8 |
| " | 10 | 56.4 |

The tetradecyl homolog is suitable as a shampoo additive, as a foam booster or stabilizer and as a hair conditioner. The hexadecyl homolog may be employed in creme rinses, as a skin or hair conditioner; and also as a textile conditioner.

The amphoteric surface-active agents of this invention are also effective in other cosmetic preparations; for example, along with an alkanolamide, such as "Super-Amide L-9-C" (Onyx Chemical Co.) for bubble-bath formulations; as emulsifying agents, in creams and lotions, and the like.

They are useful auxiliaries in textile processing. In dye baths, they serve as dye-levelers, penetrating agents, and lubricating agents for all fibers. After dyeing, the lubricating and softening characteristics carry over to serve to advantage in yarn-winding and sewability, and for all-over reduction of softening agent needed in the finishing operation.

For example, 1% to 2% of a 40% solution on the weight of the fabric, applied in the dyebox, prevents crock-marks, chafe and crow's feet on acetate or rayon. On nylon/cotton, 3% on the weight of the fabric provides leveling and penetration in dyeing.

For acrylic package pressure dyeing, 5% to 7% on the weight of the fabric serves to provide a more uniform dyeing, the higher percentages for light shades, the lower for darker shades.

These amphoterics, and especially those of higher molecular weight, serve at 0.5% to 1.0% add-on as softeners for cotton, rayon and most synthetics; with normal fulling agents such as soap they offer a more lubricated "handle", especially on wool.

Since they are amphoteric in nature, they may be used as a self-finish, at 1/2% to 3/4% solids add-on; or they may be used in combination with aminoplast resins as a plasticizer.

They are effective corrosion inhibitors for metals, and hence they may be incorporated with aerosol formulations. Along with mineral acids such as, for example, phosphoric, they are useful as metal cleaning compounds.

They may be compounded with alkalis, including caustic soda and other agents to make heavy duty industrial cleaning agents. Along with such other agents as alkylaryl sulfonates, alkanolamides and polyphosphates or silicates, they may be compounded as all purpose cleaners. With the aid of a thickening agent such as the modified celluloses and an alkali, they make effective over cleaners.

Because of their amphoteric character, they may be combined with quaternary ammonium germicides on the one hand, or with phenols.

The extremely powerful inhibitory action against Gram positive bacteria is demonstrated by the following.

EXAMPLE 14

Sodium N-2-hexadecyl-β-aminopropionate was tested for its ability to inhibit Gram positive bacteria. The minimum inhibitory concentration (MIC) level was determined as follows.

One ml. of aqueous chemical solution prepared at ten times the test concentration was added aseptically to 9 ml. of sterile nutrient broth. In this manner a series of experimental dilutions of the chemical was prepared for testing against Staphylococcus aureus. Similarly, a series of identical concentration levels in sterile TSB broth was prepared for testing Streptococcus faecalis.

Each series was inoculated with 0.1 ml. of a 1:10 sterile nutrient broth, or sterile TSB broth (TSB is Tryptic Soy Broth) dilution of a 24 hour broth culture of the test organism. The inoculated broth tubes were incubated at 37°C for 72 hours, after which the tubes were examined for macroscopic growth.

The absence of growth indicates bacteriostatic activity of the sodium-N-2-hexadecyl-β-aminopropionate. The lowest concentration of chemical which prevents growth of a bacterial species is designated as the MIC level of the chemical toward the species. The MIC of sodium-N-2-hexadecyl-β-aminopropionate toward the two Gram positive bacterial species were as follows:

| | |
|---|---|
| S. aureus | 10 ppm |
| S. faecalis | 10 ppm |

This concentration is considerably lower than the usual acceptable concentrations for bacterial inhibition. This is a most unexpected result.

Their foam-boosting properties for other surfactants and their wetting properties are amply illustrated in the foregoing Tables.

The invention claimed is:

1. The compound substantially free from metal halide having the formula:

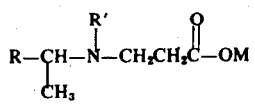

wherein R is a straight chain alkyl having from 6 to 16 carbon atoms, R' is a lower alkyl, and M is selected from the group consisting of hydrogen, alkali metal, mono-, di-, or tri-ethanolamine, and mono-, di-, or tri-propanolamine.

2. The compound of claim 1 wherein R' is selected from the group consisting of methyl and ethyl.